US007112442B2

(12) United States Patent
Rice et al.

(10) Patent No.: US 7,112,442 B2
(45) Date of Patent: *Sep. 26, 2006

(54) PEPTIDES FOR GENE DELIVERY

(75) Inventors: Kevin Gerard Rice, Ann Arbor, MI (US); Manpreet S. Wadhwa, Spring, TX (US)

(73) Assignee: The Regents of the University of Michigan, Ann Harbor, MI (US)

( * ) Notice: Subject to any disclaimer, the term of this patent is extended or adjusted under 35 U.S.C. 154(b) by 465 days.

This patent is subject to a terminal disclaimer.

(21) Appl. No.: 10/108,844

(22) Filed: Mar. 28, 2002

(65) Prior Publication Data

US 2003/0170894 A1    Sep. 11, 2003

Related U.S. Application Data

(63) Continuation of application No. 09/050,811, filed on Mar. 30, 1998, now Pat. No. 6,387,700, which is a continuation-in-part of application No. 08/743,269, filed on Nov. 4, 1996, now abandoned.

(51) Int. Cl.
    C12N 15/79   (2006.01)
    C12N 15/87   (2006.01)
    C12Q 1/68    (2006.01)
    C07N 7/00    (2006.01)
    C07N 14/00   (2006.01)

(52) U.S. Cl. .................. 435/455; 435/6; 435/320.1; 530/300; 530/324; 530/325; 530/326; 530/327; 530/328; 530/329; 538/330; 538/331

(58) Field of Classification Search .............. 435/6, 435/320.1, 455; 514/44; 530/300, 324–331
See application file for complete search history.

(56) References Cited

U.S. PATENT DOCUMENTS

| 5,166,320 A | 11/1992 | Wu et al. ............... 530/395 |
| 5,270,300 A | 12/1993 | Hunziker ............... 514/12 |
| 5,298,422 A | 3/1994 | Schwartz et al. ......... 435/320.1 |
| 5,304,121 A | 4/1994 | Sahatjian ............... 604/53 |
| 5,324,775 A | 6/1994 | Rhee et al. ............. 525/54.2 |
| 5,354,844 A | 10/1994 | Beug et al. ............. 530/345 |
| 5,460,831 A | 10/1995 | Kossovsky et al. ........ 424/493 |
| 5,464,650 A | 11/1995 | Berg et al. ............. 427/2.3 |
| 5,470,829 A | 11/1995 | Prisell et al. ........... 514/12 |
| 5,545,135 A | 8/1996 | Iacob et al. ............ 604/96 |
| 5,580,859 A | 12/1996 | Felgner et al. .......... 514/44 |
| 5,593,974 A | 1/1997 | Rosenberg et al. ....... 514/44 |
| 5,635,383 A | 6/1997 | Wu et al. ............... 435/172.3 |
| 5,674,192 A | 10/1997 | Sahatjian et al. ........ 604/28 |
| 5,674,703 A | 10/1997 | Woo et al. ............. 435/69.1 |
| 5,693,622 A | 12/1997 | Wolff et al. ............ 514/44 |
| 5,698,531 A | 12/1997 | Nabel et al. ........... 514/44 |
| 5,707,969 A | 1/1998 | Nabel et al. ........... 514/44 |
| 5,723,119 A | 3/1998 | Schwartz et al. ........ 424/85.2 |
| 5,736,392 A | 4/1998 | Hawley-Nelson et al. .......... 435/320.1 |
| 5,763,416 A | 6/1998 | Bonadio et al. .......... 514/44 |
| 5,770,580 A | 6/1998 | Ledley et al. ........... 514/44 |
| 5,874,297 A | 2/1999 | Wu et al. ............... 435/320.1 |
| 5,879,713 A | 3/1999 | Roth et al. ............. 424/489 |
| 6,387,700 B1 | 5/2002 | Rice et al. ............. 435/455 |
| 6,770,740 B1 | 8/2004 | Rice et al. ............. 530/300 |

FOREIGN PATENT DOCUMENTS

| EP | 0 190 833 | 8/1986 |
| WO | WO 90/11092 | 10/1990 |
| WO | WO9 3/21969 | 11/1993 |
| WO | WO 95/24929 | 9/1995 |
| WO | WO 96/20698 | 7/1996 |
| WO | WO 97/38729 | 10/1997 |
| WO | WO 97/46100 | 12/1997 |
| WO | WO 97/47254 | 12/1997 |
| WO | WO 98/19711 | 5/1998 |

OTHER PUBLICATIONS

Mountain, A., "Gene therapy: the first decade," Trends in Biotechnology 18: 119-128, Mar. 2000.*
Verma et al., "Gene therapy—promises, problems, and prospects," Nature 389: 239-242, Sep. 18, 1997.*
Orkin et al., Report and Recommendations of the Panel to Assess the NIH Investment in Research on Gene Therapy, issued by the U.S. National Institutes of Health, Dec. 7, 1995.*
Boulikas and Martin, "Histones, Protamine, and Polylysine but not Poly(E:K) Enhance Transfection Efficiency," *International Journal of Oncology*, 10(2):317-322, 1997, abstract only.
Eisen, et al., "Enhanced Efficiency of *In Vivo* Gene Transfer into the Thymus in Rats Using Polylysine-Folate Transfection Vectors," *Clin. Res.*, 42(3), 443A, 1994.
Schulz and Schirmer, "Principles of Protein Structure," *Springer-Verlag New York*, pp. 12-13, 1979.
Wadhwa et al., "Peptide-Mediated Gene Delivery: Influence of Peptide Structure on Gene Expression," *Bioconjugate Chem.*, 8:81-88, 1997.

(Continued)

Primary Examiner—Scott D. Priebe
(74) Attorney, Agent, or Firm—Marshall, Gerstein & Borun LLP

(57) ABSTRACT

Compositions and methods are described for nucleic acid formulation for gene delivery. A new class of low molecular weight condensing agents, namely aromatic amino acid—containing peptides, are described for use in receptor-mediated and nonreceptor-mediated gene delivery, both in vivo and in vitro.

30 Claims, 5 Drawing Sheets

OTHER PUBLICATIONS

Williams, et al., "The Primary Structure of Hen Ovotransferrin," *Eur. J. Biochem.*, 122:297-303, 1982.

Official Action for parent U.S. Appl. No. 08/743,269, filed, Nov., 4, 1996.

International Search Report for PCT/US97/19621, mailed Jan., 30, 1998.

Fang et al., "Stimulation of New Bone Formation by Direct Transfer of Osteogenic Plasmid Genes," *Proc. Natl. Acad. Sci. USA*, 93:5753-5758, 1996.

International Search Report for PCT/US99/08884, mailed Aug., 27, 1999.

Shimizu, et al., "Chrondrocyte Migration to Type I collagen, Type II Collagen and Fibronectin", *Cell Struct. and Func.*, 20(6):584, 1995.

Official Action for U.S. Appl. No. 09/469,523, mailed Mar. 23, 2000.

Adami and Rice, "Metabolically Stabilized Peptide/DNA Formulations for Enhanced Gene Expression," *Pharm. Sci., 1998 AAPS Annual Meeting, vol. 1*, S-286-S-287, 1998.

Choi et al., "Lactose-Poly(Ethylene Glycol)-Grafted Poly-L-Lysine as Hepatoma Cell-Targeted Gene Carrier," *Bioconjugate Chem.*, 9:708-718, 1998.

Midoux and Monsigny, "Efficient Gene Transfer by Histidylated Polylysine/pDNA Complexes," *Bioconjugate Chem.*, 10:406-411, 1999.

Adami et al., "Stability of Peptide-Condensed Plasmid DNA Formulations," *J. Pharm. Sci.*, 87(6):678-683, 1998.

Gottschalk et al., "A Novel DNA-Peptide Complex for Efficient Gene Transfer and Expression in Mammalian Cells," *Gene Therapy*, 3:448,457, 1996.

Katayose and Kataoka, "Water-Soluble Polyion Complex Associates of DNA and Poly(Ethylene Glycol)-Poly (L-Lysine) Block Copolymer," *Bioconjugate Chem.*, 8:702-707, 1997.

Kwok et al., "Formulation of Highly Soluble Poly(Ethylene Glycol)-Peptide DNA Condensates," *J. Pharm. Sci.*, 88(10):996-1003, 1999.

Langer and Folkman, "Polymers for the Sustained Release of Proteins and Other Macromolecules," *Nature*, 263:797-799, 1976.

Ledley, "Somatic Gene Therapy for Human Disease: Background and Prospects," *J. Pediatrics*, 110:1-8, 1987.

Midoux et al., "Specific Gene Transfer Mediated by Lactosylated Poly-L-Lysine Into Hepatoma Cells," *Nucleic Acids Res.*, 21(4):871-878, 1993.

Nicolau et al., "*In Vivo* Expression of Rat Insulin After Intravenous Administration of the Liposome-Entrapped Gene for Rat Insulin I," *Proc. Natl. Acad. Sci. USA*, 80:1068-1072, 1983.

Smith et al., "Synthetic Peptide-Based DNA Complexes for Non-viral Gene Delivery," *Advanced Drug Delivery Reviews*, 30:115-131, 1998.

Wadhwa et al., "Targeted Gene Delivery with a Low Molecular Weight Glycopeptide Carrier" *Bioconjugate Chem.*, 6:283-291, 1995.

Wasan et al., "Plasmid DNA is Protected Against Ultrasonic Cavitation-Induced Damage when Complexed to Cationic Liposomes," *J. Pharm. Sci.*, 85(4):427-433, 1996.

Wolfert et al., "Characterization of Vectors for Gene Therapy Formed by Self-Assembly Of DNA with Synthetic Block Co-Polymers," *Human Gene Therapy*, 7(10):2123-2133, 1996.

\* cited by examiner

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 1:

Cys Trp Lys Lys Lys Lys Lys Lys Lys Lys Lys Lys Lys Lys Lys
1               5                   10                  15

Lys Lys Lys Lys
            20

(2) INFORMATION FOR SEQ ID NO: 2:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 2:

Lys Lys Lys Lys Lys Lys Lys Lys Lys Lys Lys Lys Lys Lys Lys Lys
1               5                   10                  15

Lys Lys Lys (2) INFORMATION FOR SEQ ID NO: 3:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: protein (ix) FEATURE:
        (A) NAME/KEY: Binding-site
        (B) LOCATION: 1

(D) OTHER INFORMATION: /note= "The residue at this
            position is bound to an Alkaloid by a Sulfide."

(xi) SEQUENCE DESCRIPTION: SEQ ID NO: 3:

Cys Trp Lys Lys Lys Lys Lys Lys Lys Lys Lys Lys Lys Lys Lys
1               5                   10                  15

Lys Lys Lys Lys
            20

(2) INFORMATION FOR SEQ ID NO: 4:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: protein (ix) FEATURE:
        (A) NAME/KEY: Binding-site
        (B) LOCATION: 1
        (D) OTHER INFORMATION: /note= "The residue at this
            position is bound to an Alkaloid by a Sulfide."

(xi) SEQUENCE DESCRIPTION: SEQ ID NO: 4:

Cys Trp Lys Lys Lys
1               5

(2) INFORMATION FOR SEQ ID NO: 5:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: protein (ix) FEATURE:
        (A) NAME/KEY: Binding-site
        (B) LOCATION: 1
        (D) OTHER INFORMATION: /note= "The residue at this
            position is bound to an Alkaloid by a Sulfide."

(xi) SEQUENCE DESCRIPTION: SEQ ID NO: 5:

Cys Trp Lys Lys Lys Lys Lys Lys Lys Lys
1               5                   10

(2) INFORMATION FOR SEQ ID NO: 6:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: linear (ii) MOLECULE TYPE: protein (ix) FEATURE:
        (A) NAME/KEY: Binding-site
        (B) LOCATION: 1
        (D) OTHER INFORMATION: /note= "The residue at this
            position is bound to an Alkaloid by a Sulfide."

(xi) SEQUENCE DESCRIPTION: SEQ ID NO: 6:

Cys Trp Lys Lys Lys Lys Lys Lys Lys Lys Lys Lys Lys Lys Lys
1               5                   10                  15

(2) INFORMATION FOR SEQ ID NO: 7:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: protein (ix) FEATURE:
        (A) NAME/KEY: Binding-site
        (B) LOCATION: 5..6
        (D) OTHER INFORMATION: /note= "The residues at these
            positions are joined together by a Disulfide bond."

(xi) SEQUENCE DESCRIPTION: SEQ ID NO: 7:

Lys Lys Lys Trp Cys Cys Trp Lys Lys Lys
1               5                   10

(2) INFORMATION FOR SEQ ID NO: 8:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: protein (ix) FEATURE:
        (A) NAME/KEY: Binding-site
        (B) LOCATION: 10..11
        (D) OTHER INFORMATION: /note= "The residues at these
            positions are joined together by a Disulfide bond."

(xi) SEQUENCE DESCRIPTION: SEQ ID NO: 8:

Lys Lys Lys Lys Lys Lys Lys Lys Trp Cys Cys Trp Lys Lys Lys
1               5                   10                  15

Lys Lys Lys Lys
            20

(2) INFORMATION FOR SEQ ID NO: 9:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: linear (ii) MOLECULE TYPE: protein (ix) FEATURE:
        (A) NAME/KEY: Binding-site
        (B) LOCATION: 15..16
        (D) OTHER INFORMATION: /note= "The residues at these
            positions are joined together by a Disulfide bond."

(xi) SEQUENCE DESCRIPTION: SEQ ID NO: 9:

Lys Lys Lys Lys Lys Lys Lys Lys Lys Lys Lys Lys Lys Trp Cys Cys
1               5                   10                  15

Trp Lys Lys Lys Lys Lys Lys Lys Lys Lys Lys Lys Lys Lys
                20                  25                  30

(2) INFORMATION FOR SEQ ID NO: 10:

(i) SEQUENCE CHARACTERISTICS:
        (A) LENGTH: 40 amino acids
        (B) TYPE: amino acid

```
      (C) STRANDEDNESS: Not Relevant
      (D) TOPOLOGY: linear (ii) MOLECULE TYPE: protein (ix) FEATURE:
      (A) NAME/KEY: Binding-site
      (B) LOCATION: 20..21
      (D) OTHER INFORMATION: /note= "The residues at these
          positions are joined together by a Disulfide bond."

(xi) SEQUENCE DESCRIPTION: SEQ ID NO: 10:

Lys Lys Lys Lys Lys Lys Lys Lys Lys Lys Lys Lys Lys Lys Lys
1               5                   10                  15

Lys Lys Trp Cys Cys Trp Lys Lys Lys Lys Lys Lys Lys Lys Lys
            20                  25                  30

Lys Lys Lys Lys Lys Lys Lys Lys
        35                  40

(2) INFORMATION FOR SEQ ID NO: 11:

(i) SEQUENCE CHARACTERISTICS:
      (A) LENGTH: 15 amino acids
      (B) TYPE: amino acid
      (C) STRANDEDNESS: Not Relevant
      (D) TOPOLOGY: linear (ii) MOLECULE TYPE: protein (xi) SEQUENCE DESCRIPTION: SEQ ID NO: 11:

Cys Trp Lys Lys Lys Lys Lys Lys Lys Lys Lys Lys Lys Lys Lys
1               5                   10                  15
```

PEPTIDES FOR GENE DELIVERY

This application is a continuation of application Ser. No. 09/050,811, filed Mar. 30, 1998, now U.S. Pat. No. 6,387,700, which is a continuation-in-part of U.S. patent application Ser. No. 08/743,269, filed Nov. 4, 1996, now abandoned.

This application was made with support awarded by the National Institutes of Health (grant number GM48049). The government has certain rights in the invention.

FIELD OF THE INVENTION

The present invention relates to the introduction of genes into cells. In particular, the present invention relates to compositions and methods of nucleic acid formulation for gene delivery.

BACKGROUND

There are a number of techniques for the introduction of genes into cells. One common method involves viruses that have foreign genes (e.g., transgenes) incorporated within the viral DNA. However, the viral genes are also delivered with the desired gene and this can lead to undesirable results.

Nonviral gene delivery systems are being developed to transfect mammalian host cells with foreign genes. In such approaches, nucleic acid is typically complexed with carriers that facilitate the transfer of the DNA across the cell membrane for delivery to the nucleus. The efficiency of gene transfer into cells directly influences the resultant gene expression levels.

The carrier molecules bind and condense DNA into small particles which facilitate DNA entry into cells through endocytosis or pinocytosis. In addition, the carrier molecules act as scaffolding to which ligands may be attached in order to achieve site specific targeting of DNA.

The most commonly used DNA condensing agent for the development of nonviral gene delivery systems is polylysine in the size range of dp 90–450. Its amino groups have been derivatized with transferrin, glycoconjugates, folate, lectins, antibodies or other proteins to provide specificity in cell recognition, without compromising its binding affinity for DNA. However, the high molecular weight and polydispersity of polylysine also contribute to a lack of chemical control in coupling macromolecular ligands which leads to heterogeneity in polylysine-based carrier molecules. This can complicate the formulation of DNA carrier complexes and limits the ability to systematically optimize carrier design to achieve maximal efficiency.

Clearly, there is a need for improved methods of gene delivery. Such methods should be amenable to use with virtually any gene of interest and permit the introduction of genetic material into a variety of cells and tissues.

SUMMARY OF THE INVENTION

The present invention relates to the introduction of genes into cells. In particular, the present invention relates to compositions and methods of nucleic acid formulation for gene delivery. The invention contemplates cationic peptides containing aromatic amino acids (i.e., phenylalanine, tyrosine and tryptophan) and in particular, tryptophan—containing peptides that mediate gene transfer by condensing DNA into small particles.

The present invention contemplates methods for introducing nucleic acid into cells (both in vivo and in vitro). In one embodiment, the method comprises a) providing: i) an aromatic amino acid—containing peptide capable of binding to nucleic acid, ii) nucleic acid encoding one or more gene products, and iii) cells capable of receiving said nucleic acid, said cells having cell membranes; b) binding said peptide to said nucleic acid to make a complex; c) introducing said complex to said cells under conditions such that said complex is delivered across said cell membrane.

While it is not intended that the invention be limited by the length of the peptide, it is preferred that the peptides of the present invention are less than forty amino acids in length, more preferably less than thirty amino acids in length, and most preferably, less than twenty amino acids in length.

It is also not intended that the present invention be limited by the precise composition of the peptides. A variety of peptides containing aromatic amino acids are contemplated. In one embodiment, the peptides of the present invention comprise L-lysine (Lys) and tryptophan (Trp). In another embodiment, the peptides of the present invention contain L-lysine (Lys), tryptophan (Trp) and cysteine (Cys). In a preferred embodiment, a peptide is contemplated that demonstrates high activity in mediating gene transfer in cell culture, said peptide having the structure (SEQ ID NO:1): Cys-Trp-(Lys)$_{18}$. Other peptides (including peptides with two, three and four tryptophan residues) are contemplated.

The present invention also contemplates the use of the peptides of the present invention in receptor-mediated gene transfer (both in vitro and in vivo). In one embodiment, the method comprises linking the DNA to a cationic peptide of the present invention (usually an aromatic amino acid—substituted poly-L-lysine) containing a covalently attached ligand, which is selected to target a specific receptor on the surface of the tissue of interest. The gene is taken up by the tissue, transported to the nucleus of the cell and expressed for varying times.

In one embodiment, the receptor-mediated method of the present invention for delivering an oligonucleotide to cells of an animal, comprises a) providing: i) a target binding moiety capable of binding to a receptor present on the surface of a cell in a tissue of an animal, ii) an aromatic amino acid—substituted polylysine capable of binding to nucleic acid, iii) an oligonucleotide encoding one or more gene products, and iv) a recipient animal having cells, said cells having said receptor; b) conjugating said target binding moiety to said substituted polylysine to form a carrier; c) coupling said carrier with said oligonucleotide to form a pharmaceutical composition; and d) administering said composition to said recipient animal under conditions such that said oligonucleotide is delivered to said cells.

As noted above, the present invention contemplates polylysine peptides containing tryptophan for use in gene delivery. In one embodiment, the synthetic peptides contemplated possess a lysine repeat varying from between 3 and 36 residues and comprise one or more tryptophan and cysteine residues. In a preferred embodiment, the peptide comprises 13–18 lysine residues; such peptides which possess a single tryptophan residue enhances gene transfer to cells in culture by up to three orders of magnitude relative to comparable polylysine peptide lacking a tryptophan.

An understanding of how the peptides of the present invention improve the gene delivery in a superior manner is not required to practice the present invention. Nonetheless, it is believed that the mechanism of peptide mediated gene transfer is related to the efficiency of condensing DNA into small particles. While not limited to any particular theory, it is believed that tryptophan plays a specific role in organizing the DNA binding of cationic peptide to produce small condensates that exhibit enhanced gene transfer efficiency. In this manner, the tryptophan—containing peptides of the present invention represent a new class of low molecular weight condensing agents that may be modified with ligands to produce low molecular weight carriers for site specific gene delivery.

It is not intended that the present invention be limited by the nature of the nucleic acid. The target nucleic acid may be native or synthesized nucleic acid. The nucleic acid may be from a viral, bacterial, animal or plant source.

DEFINITIONS

To facilitate understanding of the invention, a number of terms are defined below.

The term "gene" refers to a DNA sequence that comprises control and coding sequences necessary for the production of a polypeptide or precursor thereof. The polypeptide can be encoded by a full length coding sequence or by any portion of the coding sequence so long as the desired activity is retained.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprised of two or more deoxyribonucleotides or ribonucleotides, usually more than three (3), and typically more than ten (10) and up to one hundred (100) or more. The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

The terms "nucleic acid substrate" and "nucleic acid template" are used herein interchangeably and refer to a nucleic acid molecule which may comprise single- or double-stranded DNA or RNA.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

The term "sequence variation" as used herein refers to differences in nucleic acid sequence between two nucleic acid templates. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene. It is noted, however, that the invention does not require that a comparison be made between one or more forms of a gene to detect sequence variations.

The "target cells" may belong to tissues (including organs) of the organism, including cells belonging to (in the case of an animal) its nervous system (e.g., the brain, spinal cord and peripheral nervous cells), the circulatory system (e.g., the heart, vascular tissue and red and white blood cells), the digestive system (e.g., the stomach and intestines), the respiratory system (e.g., the nose and the lungs), the reproductive system, the endocrine system (the liver, spleen, thyroids, parathyroids), the skin, the muscles, or the connective tissue.

Alternatively, the cells may be cancer cells derived from any organ or tissue of the target organism, or cells of a parasite or pathogen infecting the organism, or virally infected cells of the organism.

Exogenous DNA has been introduced into hepatocytes by targeting the asialoglycoprotein (ASGP) receptor by means of a ligand-poly-L-lysine bioconjugate. See U.S. Pat. No. 5,166,320, hereby incorporated by reference. Such receptor-mediated approaches can be used in combination with the novel peptides of the present invention.

Exogenous DNA has also been introduced for antisense treatment. See U.S. patent application Ser. No. 08/042,943, filed Apr. 5, 1993 (now abandoned) and corresponding PCT Publication No. WO 94/23050, hereby incorporated by reference. Such antisense approaches can be used in combination with the novel peptides of the present invention.

DESCRIPTION OF THE DRAWINGS

FIG. 3A depicts the results for HepG2 cells while FIG. 3B shows the results of COS 7 cells.

DESCRIPTION OF THE INVENTION

Figure 1A:
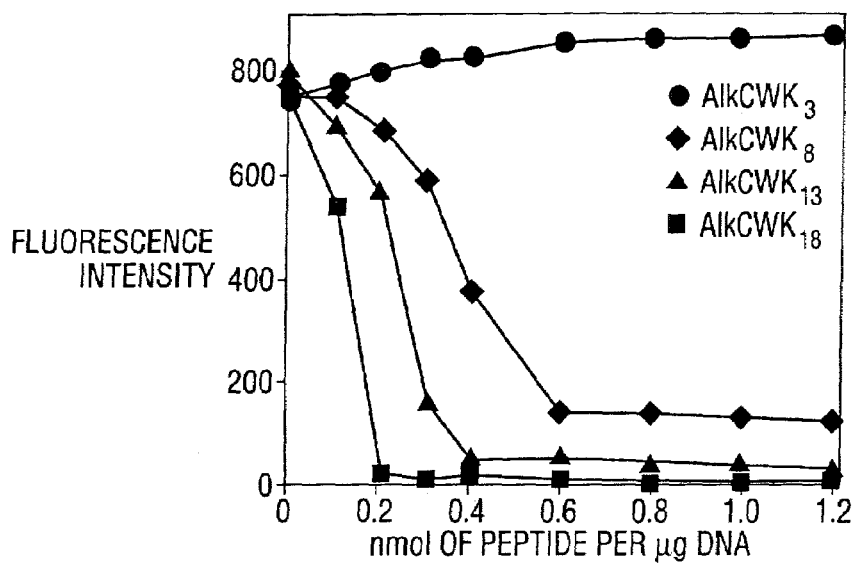
FIGS. 1A, 1B, 1C, 1D, 1E and 1F graphically depict light scattering results for peptides of the present invention (each titration represents the average of three determinations).

The present invention relates to the introduction of genes into cells. In particular, the present invention relates to compositions and methods of nucleic acid formulation for gene delivery. The aromatic amino acid—containing peptides of the present invention represent a new class of low molecular weight condensing agents for gene delivery.

Cationic peptides possessing a single cysteine, tryptophan and a lysine repeat were synthesized to define the minimal peptide length needed to mediate transient gene expression in mammalian cells. The N-terminal cysteine in each peptide was either alkylated or oxidatively dimerized to produce peptide possessing lysine chains of 3, 6, 8, 13, 16, 18, 26, and 36 residues. Each synthetic peptide was studied for its ability to condense plasmid DNA and compared to (SEQ ID NO:2) polylysine$_{19}$ and cationic lipids to establish relative in vitro gene transfer efficiency in HepG2 and COS 7 cells.

Peptides with lysine repeats of 13 or more bound DNA tightly and produced condensates that decreased in mean diameter from 231 nm down to 53 nm as the lysine chain length increased. In contrast, peptides possessing 8 or fewer lysine residues were similarly to polylysine$_{19}$ which bound DNA weakly and produced large (0.7–3 μm) DNA condensates.

The luciferase expression was elevated a thousand-fold after transfecting HepG2 cells with DNA condensates prepared with (SEQ ID NO:3) alkylated Cys-Trp-Lys$_{18}$ and cationic lipids were equivalent in HepG2 cells but different by ten-fold in COS 7 cells.

A forty-fold reduction in particle size and a thousand-fold amplification in transfection efficiency for (SEQ ID NO:3) AlkCWK$_{18}$ DNA condensates relative to (SEQ ID NO:2) polylysine$_{19}$ DNA condensates suggests a contribution from tryptophan that leads to enhanced gene transfer properties for (SEQ ID NO:3) AlkCWK$_{18}$ Tryptophan containing cationic peptide result in the formation of small DNA condensates that mediate efficient nonspecific gene transfer in mammalian cells. Due to their low toxicity, these peptide may find utility as carriers for nonspecific gene delivery or may be developed further as low molecular weight DNA condensing agents used in targeted gene delivery systems.

EXPERIMENTAL

The following examples serve to illustrate certain preferred embodiments and aspects of the present invention and are not to be construed as limiting the scope thereof.

In the experimental disclosure which follows, the following abbreviations apply: ° C. (Centigrade); μg (micrograms); μmole (micromoles); μl (microliters); mL (milliliters); mM (milliMolar); RP-HPLC (reverse phase high performance liquid chromatography); CWK (cysteine-tryptophane-lysine; TFA (trifluoroacetic acid); EDF (ethanedithiol); MALDI-TOF-MS (matrix assisted time of flight mass spectrometry); RLU (relative light units); DTT (dithiothreitol); FBS (fetal bovine serum); MEM (minimal essential media); DMEM (Dulbecco's modified Eagel media); HBM (Hepes buffered mannitol); QELS (quasi elastic light scattering).

In the examples described below, N-terminal Fmoc protected amino acids, and all other reagents for peptide synthesis were obtained from Advanced ChemTech (Lexington, Ky.). Minimum essential media (MEM), Sephadex G25, dithiothreitol, iodoacetamide, iodoacetic acid and polylysine$_{19}$ (MW 1000–4000) were purchased from Sigma Chemicals (St. Louis, Mo.). Ethanedithiol (EDT) was purchased from Aldrich Chemical (Milwaukee, Wis.). Trifluoroacetic acid (TFA) was purchased from Fisher Scientific (Pittsburgh, Pa.). LB media, LB agar, D-luciferin, and luciferase from *Photinus pyralis* (EC 1.13.12.7) were obtained from Boehringer Mannheim (Indianapolis, Ind.). HepG2 and COS 7 cells were from the American Type Culture Collection (Rockville, Md.). Dulbecco's modified Eagle medium (DMEM), media supplements and heat inactivated "qualified" fetal bovine serum (FBS) were from Gibco BRL (Grand Island, N.Y.). Bradford reagent was purchased from BioRad (Hercules, Calif.) and thiazole orange was a gift from Beckton Dickinson Immunocytometry Systems (San Jose, Calif.). The 5.6 kbp plasmid pCMVL encoding the reporter gene luciferase under the control of the cytomegalovirus promoter was a gift from Dr. M. A. Hickman at the University of California, Davis. Peptide purification was performed using a semi-preparative (10 μm) C18 RP-HPLC column from Vydac (Hesperia, Calif.). HPLC was performed using a computer interfaced HPLC and fraction collector from ISCO (Lincoln, Nebr.).

Plasmid DNA was prepared by the alkaline lysis method and purified on cesium chloride gradient. Peptide were prepared by solid phase peptide synthesis on Fmoc-L-Boc-lysine-Wang resin (p-benzyloxybenzyl alcohol resin, 1% divinyl benzene cross linked, 100–200 mesh) at a 136 μmol scale (0.68 mmol/g resin).

Peptide DNA condensates were prepared at a final DNA concentration of 20 μg/ml and at a peptide/DNA stoichiometry varying from 0.1 to 1.5 nmol of peptide per μg of DNA. The condensates were formed by adding peptide (2–30 nmol) prepared in 500 μl of isotonic Hepes buffered mannitol (HBS, 0.27 M mannitol, 5 mM sodium Hepes, pH 7.5) to 20 μg of DNA in 500 μl HBM while vortexing, followed by equilibration at room temperature for 30 min.

Sedimentation of DNA condensates was evaluated by measuring the concentration of DNA in solution before and after centrifugation. After forming peptide DNA condensates as described above, a 50 μl aliquot (1 μg of DNA) was diluted in 1 ml of water and the Abs$_{260\ nm}$ was determined on a Beckman DU640 spectrophotometer. Following centrifugation at 13,000 g for 4 min at room temperature an identical aliquot was diluted with 1 ml of water and the concentration of DNA remaining in solution was determined. The ratio of absorbances subtracted from unity and multiplied by 100 was defined as the percent sedimentation.

Peptide binding to DNA was monitored by a fluorescence titration assay. A 1 μg aliquot of the peptide DNA condensate prepared as described above was diluted to 1 ml in HBM containing 0.1 μM thiazole orange. The fluorescence of the intercalated dye was measured on an LS50B fluorometer (Perkin Elmer, UK) in a micro cuvette by exciting at 500 nm while monitoring emission at 530 nm, with the slits set at 15 and 20 nm and photomultiplier gain set to 700 volts. DNA condensation was monitored by measuring total scattered light at 90° by setting both monochromators to 500 nm and decreasing slit widths to 2.5 nm. Fluorescence and scattered light intensity blanks were subtracted from all values before data analysis.

Transmission electron microscopy was preformed by immobilizing condensed DNA on carbon coated copper grids (3 mm diameter, 400 mesh; Electron Microscopy Sciences, Fort Washington, Pa.). Grids were glow discharged and 3 μl of peptide DNA condensate (20 μg/ml), prepared as described above, was placed on the grid for 5 min. The grids were blotted dry then stained by floating for 1.5 min on each of three 100 μl drops of urinal acetate (1%, in 95% ethanol) followed by rinsing with 0.4% detergent solution (PhotoFlo, Kodak), and drying. Electron microscopy was performed using a Philips EM-100 transmission electron microscope.

Particle size analysis was measured for peptide DNA condensates prepared at a DNA concentration of 20 μg of DNA. Samples were analyzed using a Nicomp 370 Autodilute submicron particle sizer in the solid particle mode and acquisition was continued until the fit error was less than ten. The mean diameter and population distribution were computed from the diffusion coefficient using functions supplied by the instrument.

EXAMPLE 1

Formulation of Peptide DNA Condensates

Cationic peptides were designed to probe the minimal size needed to mediate efficient gene transfer in mammalian cells. The synthetic strategy involved comparison of four peptides with varying lysine chain length in the range of 3–18 residues. During peptide synthesis, truncated peptides were capped by N-acetylation and a tryptophan residue was placed near the N-terminus to provide a chromophore for identification of full length sequences during purification. This residue allows quantitation of peptide concentration and is also intended for use in monitoring fluorescence to evaluate peptide binding to DNA as previously described. In addition, each peptide possessed an N-terminal cysteine residue as a potential ligand attachment site.

The synthesis was accomplished using a computer interfaced Model 90 synthesizer from Advanced Chemtech, Lexington, Ky. Lysine and tryptophan side chains were Boc protected and the sulfhydryl side chain of cysteine was protected with a trityl group. A six molar excess of N-terminal Fmoc protected amino acid was activated in situ in the reaction vessel by adding equimolar diisopropylcarbodiimide and N-hydroxybenzotriazole in a total reaction volume of 18 ml. Coupling was carried out for 1 hr and was followed with a capping cycle for 30 min with 10% acetic anhydride in 1% diisopropylethylamine. Fmoc deblocking was performed with 25% piperidine for 12 min. All reagents were dissolved in dimethyl formamide.

At completion, the resin conjugated peptide was washed with dichloromethane, dried and weighed. Cleavage was performed in a solution of TFA:EDT:water (95:2.5:2.5 v/v) for 30 min at room temperature, which simultaneously deprotected the amino acid side chains. The peptide solution was extracted with diethyl ether, concentrated by rotary evaporation, and freeze dried. Lyophilized crude peptide were dissolved in degassed and nitrogen purged 0.1% TFA. Peptide (3 µmol per injection) were purified on a semi-preparative (2×25 cm) C18 RP-PHPLC column eluted at 10 ml/min with 0.1% TFA and acetonitrile (5–20% over 40 min) while monitoring absorbance at 280 nm, 1.0 AUFS. Purified peptide were concentrated by rotary evaporation, lyophilized, and stored dry at −20° C.

Lyophilized peptide (1 µmol) were dissolved in 1 ml of nitrogen purged 50 mM Tris hydrochloride (pH 7.5) and reduced by the addition of 250 µl of 100 mM dithiothreitol prepared in the same buffer by reacting at room temperature for 30 min. Alkylation was carried out by adding 25 mg of solid iodoacetamide or iodoacetic acid followed by reacting for 1 hour at room temperature. The alkylated peptide were acidified to pH 2.0 with TFA and purified by RP-HPLC as described above. The yield of each purified peptide (approx. 25%) was determined from the absorbance of tryptophan ($\epsilon_{280\,nm}$=5600 M$^{-1}$cm$^{-1}$). The TFA salt of polylysine$_{19}$ was prepared by chromatographing the hydrobromide salt on RP-HPLC eluted with 0.1% TFA and acetonitrile while detecting 214 nm as described above. The concentration of polylysine$_{19}$ was established by fluorescamine analysis using a calibrated standard of (SEQ ID NO:3) AlkCWK$_{18}$ as a reference.

Dimeric peptides were prepared by dissolving 1 µmol of each purified CWK$_n$ (n=3,8,13, or 18) peptide in Tris hydrochloride pH 7.5 followed by reaction at 37° C. for 24 hrs. Each dimeric peptide was purified using RP-HPLC as described above and quantified by Abs$_{280\,nm}$ ($\epsilon$=11,200 M$^{-1}$ cm$^{-1}$).

Peptides were alkylated with iodacetamide to provide (SEQ ID NO:4; SEQ ID NO:5; SEQ ID NO:6; SEQ ID NO:3) AlkCWK$_n$ (where n=3, 8, 13 or 18 residues) (Table I). A further extension of this peptide series was accomplished by allowing the cysteine of each monomeric peptide to oxidize, resulting in a panel of homodimeric peptides each possessing two tryptophans and a discontinuous lysine repeat of

TABLE I

Peptides For Gene Delivery

| Name | Sequence | Mass (Obs./Calc$^a$) |
|---|---|---|
| AlkCWK$_3$ | Alk-S-Cys-Trp-(Lys)$_3$ (SEQ ID NO:4) | 750.2/750.0 |
| AlkCWK$_8$ | Alk-S-Cys-Trp-(Lys)$_8$ (SEQ ID NO:5) | 1391.1/1390.9 |
| AlkCWK$_{13}$ | Alk-S-Cys-Trp-(Lys)$_{13}$ (SEQ ID NO:6) | 2031.1/2031.8 |
| AlkCWK$_{18}$ | Alk-S-Cys-Trp-(Lys)$_{18}$ (SEQ ID NO:3) | 2672.7/2672.5 |
| DiCWK$_3$ | (Lys)$_3$-Trp-Cys-S-S-Cys-Trp-(Lys)$_3$ (SEQ ID NO:7) | 1382.5/1382.8 |
| DiCWK$_8$ | (Lys)$_8$-Trp-Cys-S-S-Cys-Trp-(Lys)$_8$ (SEQ ID NO:8) | 2664.5/2665.2 |
| DiCWK$_{13}$ | (Lys)$_{13}$-Trp-Cys-S-S-Cys-Trp-(Lys)$_{13}$ (SEQ ID NO:9) | 3946.2/3945.9 |
| DiCWK$_{18}$ | (Lys)$_{18}$-Trp-Cys-S-S-Cys-Trp-(Lys)$_{18}$ (SEQ ID NO:10) | 5227.8/5227.9 |
| Polylysine$_{19}$ | (Lys)$_{19}$ (SEQ ID NO:2) | n.d$^b$/2435.8 |

$^a$Masses are calculated as the average M + 1 of the free base.
$^b$The mass of polylysine$_{19}$ was not determined due to polydispersity.

either 6, 16, 26, or 36 residues in length (Table I). Substitution of iodoacetic acid for iodacetamide in the alkylation step led to an (SEQ ID NO:3) AlkCWK$_{18}$ peptide that was acid stable and was functionally equivalent in formulation and biological assays.

Peptide were characterized using MALDI-TOF-MS which produced a dominant ion corresponding to the anticipated molecular weight of each peptide (Table I). The peptide (1 nmol) was reconstituted in 100 µl of 0.1% acetic acid and 1 µl was applied to the target and analyzed using a Vestec-2000 internal standard. The instrument was operated with 23 KV ion accelerating voltage and a 3 KV multiplier voltage using a 337 nm VSL-SS&ND nitrogen laser with a 3 ns pulse width.

Peptides were studied for DNA binding using a dye exclusion assay. Peptide binding to DNA leads to exclusion of thiazole orange intercalation and a decrease in fluorescence. Titration of (SEQ ID NO:4; SEQ ID NO:5; SEQ ID NO:6; SEQ ID NO:3) AlkCWK$_{3,\,8,\,13,\,or\,18}$ with DNA in the range of 0.1–1.5 nmol of peptide per µg of DNA led to a reduction in fluorescence except for the smallest peptide (SEQ ID NO:4) (AlkCWK$_3$) which failed to exclude the intercalator within the titration range (FIG. 1A). An asymptote in the fluorescence decline was observed at a stoichiometry of 0.6, 0.4 or 0.2 nmol of peptide per µg of DNA for (SEQ ID:5; SEQ ID NO:6; SEQ ID NO:3) AlkCWK$_{8,\,13,\,or\,18}$, respectively (FIG. 1A). The relative fluorescence intensity at peptide/DNA stoichiometries above the asymptote established that (SEQ ID NO:6; SEQ ID NO:3) AlkCWK$_{13 \text{ and } 18}$ were able to exclude thiazole orange intercalation more efficiently than (SEQ ID NO:5) AlkCWK$_8$.

Figure 1B:
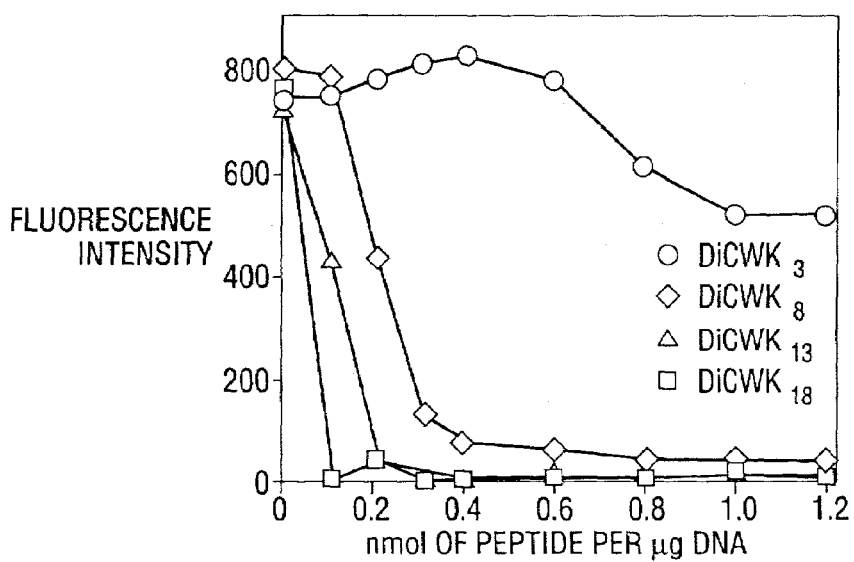

Dimeric peptides (SEQ ID NO:7; SEQ ID NO:8; SEQ ID NO:9; SEQ ID NO:10) (DiCWK$_n$, n=8, 13, 18) also possessed high affinity for DNA as evidenced by the stoichiometry of the fluorescence asymptote and the reduction is residual fluorescence, both of which correlated with the number of lysine residues (FIG. 1B). Of this series (SEQ ID NO:7), DiCWK$_3$ possessed weak affinity for DNA and thereby produced an asymptote at a stoichiometry of 1 nmol of peptide per μg of DNA.

Figure 1C:
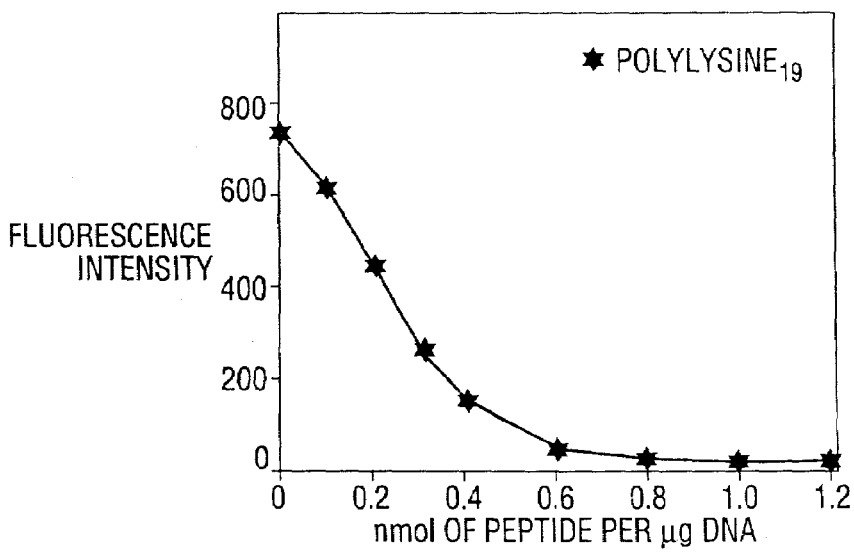

In contrast to these results, polylysine$_{19}$ demonstrated a markedly different fluorescence titration curve compared to the alkylated or dimeric peptides of comparable length (FIG. 1C). Even though (SEQ ID NO:2) polylysine$_{19}$ has a similar number of lysine residues as (SEQ ID NO:3) AlkCWK$_{18}$ its fluorescence asymptote occurs at a stoichiometry of approximately 0.6 mmol of peptide per μg of DNA. This result suggests that polylysine$_{19}$ binding to DNA is weak relative to (SEQ ID NO:3) AlkCWK$_{18}$.

Figure 1D:
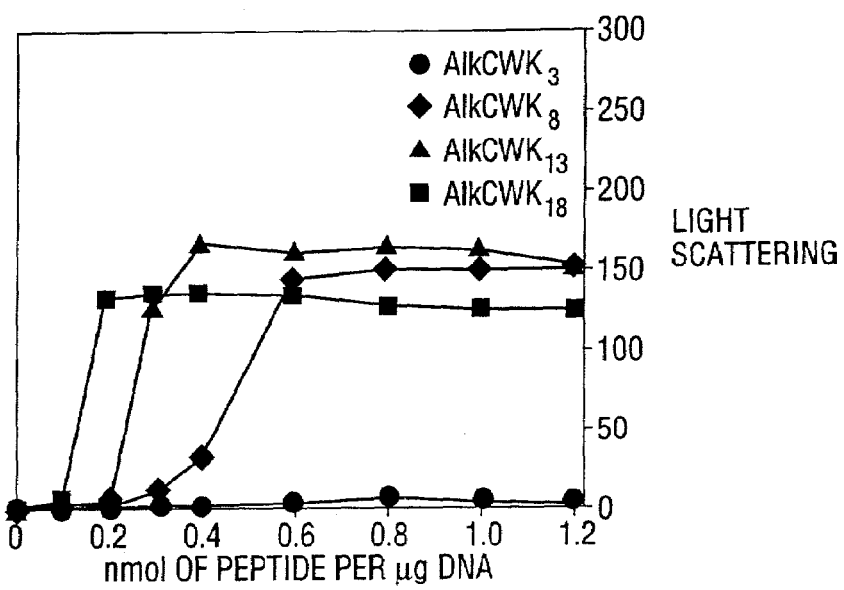

Total light scattering at 90° was used to detect the peptide stoichiometry at which condensed DNA particles were formed. Titration of either (SEQ ID NO:5; SEQ ID NO:6; SEQ ID NO:3) AlkCWK$_{8, 13, \text{ or } 18}$ with DNA produced a maximal total light scattering at stoichiometries that corresponded to the asymptote observed in the fluorescence exclusion assay (FIG. 1D). A plateau in the light scattering profile observed at a stoichiometry of 0.6, 0.4, and 0.2 for AlkCWK$_{8, 13, \text{ or } 18}$, respectively, established the complete condensations of DNA at or above this peptide/DNA ratio. In contrast, titration of DNA with AlkCWK$_3$ failed to produce an increase in the light scattering, supporting earlier observations that indicate AlkCWK$_3$ fails to bind to DNA.

Figure 1E:
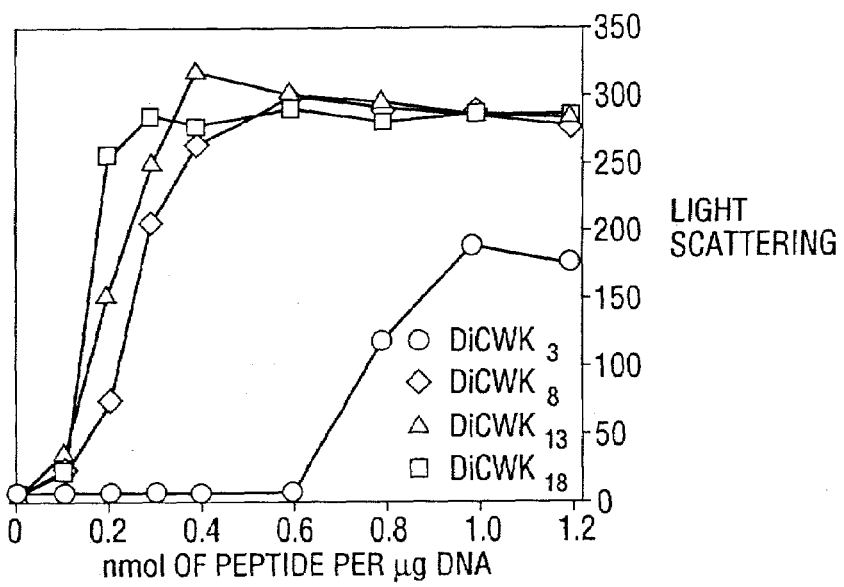

Titration of the dimeric peptides with DNA each produced condensates detected by light scattering (FIG. 1E). Although the plateau light scattering level for each dimeric peptide DNA condensate was nearly indistinguishable, the stoichiometry at which the plateau was achieved occurred at 0.6, 0.4, and 0.2 mmol of peptide per μg of DNA for (SEQ ID NO:8; SEQ ID NO:9; SEQ ID NO:10) DiCWK$_{8, 13, \text{ and } 18}$, respectively. A weaker binding affinity for (SEQ ID NO:7) DiCWK$_3$ was evident from the plateau in light scattering which occurred at a stoichiometry of 1 nmol per μg of DNA (FIG. 1E).

Figure 1F:
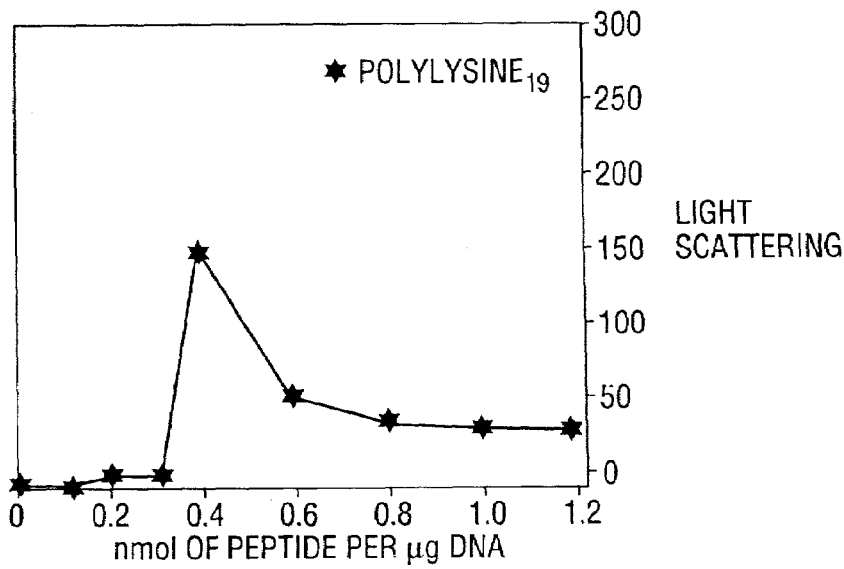

The light scattering profile for polylysine$_9$ was very distinct from that obtained for alkylated and dimeric peptides. A sharp increase occurred at a stoichiometry of 0.4 nmol per μg of DNA which declined to approximately 50 light scattering units at higher peptide/DNA stoichiometries (FIG. 1F). This light scattering titration profile distinguished the binding properties of (SEQ ID NO:2) polylysine$_{19}$ from (SEQ ID NO:11) CWK$_{13}$ peptides, suggesting differences in the particle size for (SEQ ID NO:2) polylysine$_{19}$ DNA condensates.

Figure 2A:
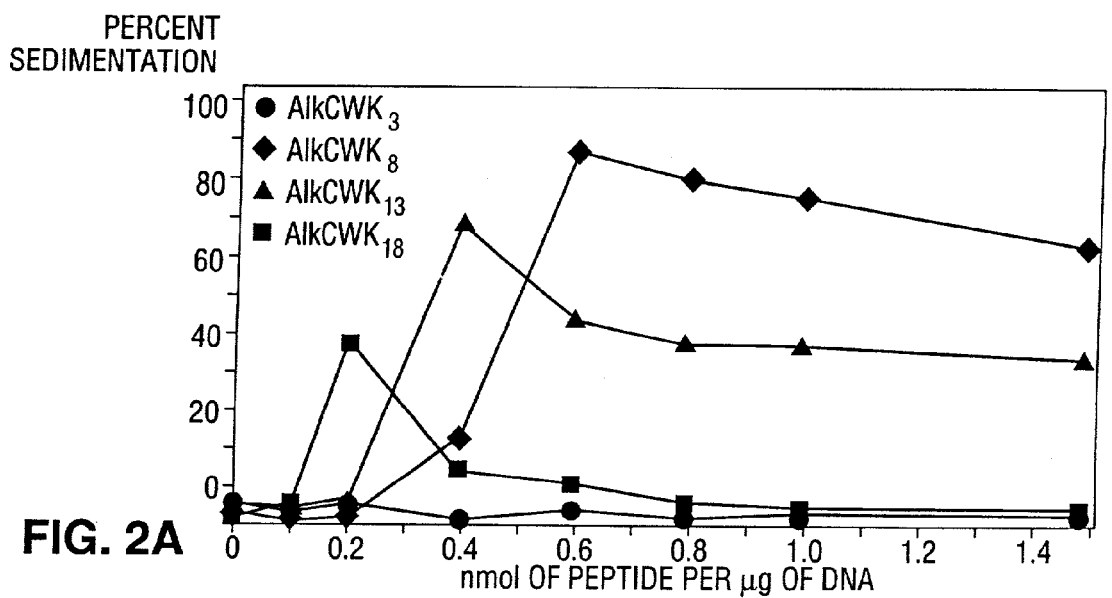
FIGS. 2A, 2B and 2C graphically show the percent of DNA sedimented following centrifugation of peptide induced DNA condensates.

To evaluate the relative particle size of DNA condensates prepared at stoichiometries ranging from 0.1–1.5 nmol of peptide per μg of DNA, a sedimentation assay was utilized to measure the DNA remaining in suspension following centrifugation at 13,000×g for 4 min (18) (FIG. 2). Titration of DNA with (SEQ ID NO:4) AlkCWK$_3$ resulted in the complete recovery of the DNA following centrifugation, supporting earlier findings that indicate AlkCWK$_3$ fails to bind and condense DNA into particles. Alternatively (SEQ ID NO:5; SEQ ID NO:6; SEQ ID NO:3), AlkCWK$_{8, 13, \text{ or } 18}$ each produced maximal sedimentation at a stoichiometry which roughly correlates with the stoichiometry calculated for a charge neutral (SEQ ID NO:5) complex (FIG. 2A). At stoichiometries greater than charge neutral, AlkCWK$_8$ condensates sedimented to a greater extent than (SEQ ID NO:6; SEQ ID NO:3) AlkCWK$_{13}$ or AlkCWK$_{18}$ condensates, indicating their larger size.

Figure 2B:
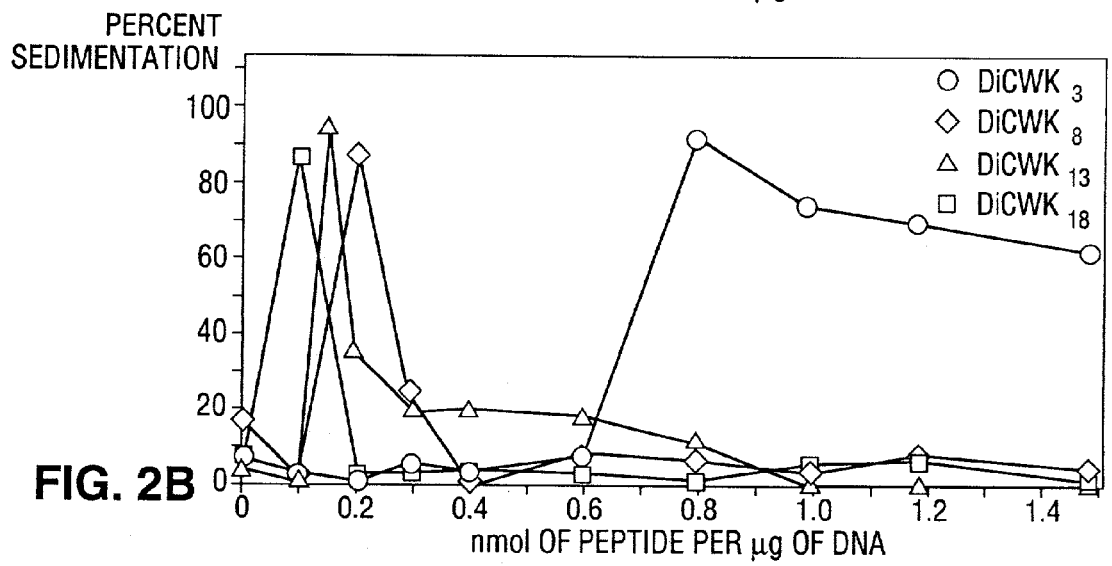

A similar trend was observed when sedimenting dimeric peptide DNA condensates. The maximal sedimentation was observed at a stoichiometry of 0.8, 0.2, 0.15 and 0.1 nmol of peptide per μg of DNA for (SEQ ID NO:7; SEQ ID NO:8; SEQ ID NO:9; SEQ ID NO:10) DiCWK$_{3, 8, 13, \text{ and } 18}$, respectively, (FIG. 2B). At stoichiometries above the calculated charge neutral point (SEQ ID NO:8; SEQ ID NO:9; SEQ ID NO:10) DiCWK$_{8, 13, \text{ and } 18}$ DNA condensates failed to sediment suggesting they are smaller in size (FIG. 2B). It is also evident that (SEQ ID NO:7) DiCWK$_3$ DNA condensates were large due to the observed sedimentation (70–80%) at stoichiometries above the charge neutralization point (FIG. 2B).

Figure 2C:
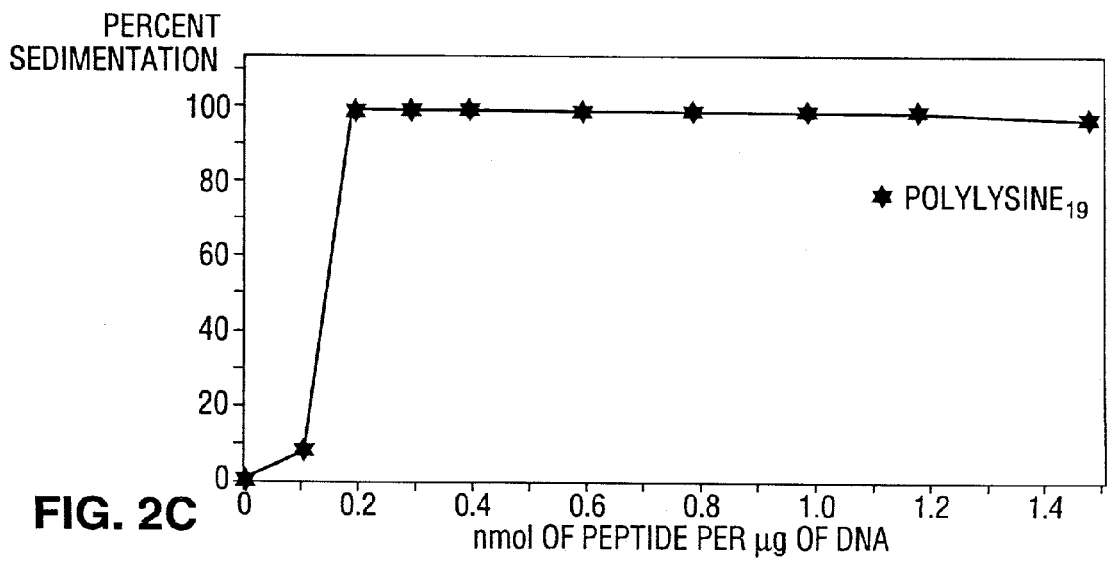

In contrast (SEQ ID NO:2), polylysine$_{19}$ DNA condensates sedimented completely at 0.2 nmol of peptide per μg of DNA and failed to recover at higher stoichiometries. These data established that once (SEQ ID NO:2) polylysine$_9$ DNA condensates are formed, they remained large throughout the titration range (FIG. 2C).

DNA condensates were prepared with alkylated peptides, dimeric peptides and polylysine$_{19}$ at a stoichiometry of 0.8 nmol of peptide per μg of DNA and particle sizes were compared using quasi elastic light scattering (QELS). A population of particles with average diameters of 0.7–3.1 μm was determined for (SEQ ID NO:2; SEQ ID NO:4; SEQ ID NO:7) polylysine$_{19}$ AlkCWK$_3$ and DiCWK$_3$ DNA condensates whereas no particles were detected for (SEQ ID NO:4) AlkCWK$_3$ DNA condensates (Table II), consistent with the results of sedimentation analysis.

Each alkylated or dimeric peptide possessing thirteen lysine residues or more produced a population of particles with mean diameters of 53–231 nm (Table II). It should be noted that particle populations were most often bimodal, possessing a major (>90%) smaller diameter population and a minor larger diameter population which contributed to the large standard deviation of the average particle size (Table II).

Particle sizes determined by QELS were substantiated by analyzing DNA condensates using electron microscopy. The images (not shown) demonstrate that condensates produced with (SEQ ID NO:3) AlkCWK$_{18}$ are relatively uniform particles with diameters of approximately 50–100 nm whereas (SEQ ID NO:2) polylysine$_{19}$ induced condensates were large flocculated particles, consistent with the result of particle size analysis by QELS.

TABLE II

QELS Particle Size Distribution

| | Particle Size Population | |
|---|---|---|
| Peptide DNA Condensate[a] | Diameter[b] (nm) | ó (nm)[c] |
| Polylysine$_{19}$ (SEQ ID NO:2) | 3102 | 297 |
| AlkCWK$_3$ (SEQ ID NO:4) | — | — |
| AlkCWK$_8$ (SEQ ID NO:5) | 2412 | 354 |
| AlkCWK$_{13}$ (SEQ ID NO:6) | 231 | 107 |
| AlkCWK$_{18}$ (SEQ ID NO:3) | 78 | 30 |

TABLE II-continued

QELS Particle Size Distribution

| Peptide DNA Condensate[a] | Particle Size Population | |
|---|---|---|
| | Diameter[b] (nm) | ó (nm)[c] |
| DiCWK$_3$ (SEQ ID NO:7) | 724 | 154 |
| DiCWK$_8$ (SEQ ID NO:8) | 53 | 24 |
| DiCWK$_{13}$ (SEQ ID NO:9) | 56 | 29 |
| DiCWK$_{18}$ (SEQ ID NO:10) | 64 | 27 |

[a]Peptide DNA condensates were prepared at a concentration of 20 µg/ml of DNA and at stoichiometry of 0.8 or 1.0 nmol (DiCWK$_3$) of peptide per µg of DNA in HBM
[b]Represents the mean diameter of particles.
[c]Standard deviation of the population.

EXAMPLE 2

In Vitro Gene Transfection

HepG2 cells (2×10$^6$ cells) were plated on 6×35 mm wells and grown to 40–70% confluency in MEM supplemented with 10% FBS, penicillin and streptomycin (10,000 U/ml), sodium pyruvate (100 mM), and L-glutamine (200 mM). Transfections were performed in MEM (2 ml per 35 mm well) with 2% FBS, with or without 80 µM chloroquine. Peptide DNA condensates (10 µg of DNA in 0.5 ml HBM) were added drop wise to triplicate wells. After 5 h incubation at 37° C., the media was replaced with MEM supplemented with 10% FBS.

Luciferase expression was determined at 24 h with some modification of a published method. Briefly, cells were washed twice with ice-cold phosphate buffered saline (calcium and magnesium free) and then treated with 0.5 ml of ice-cold lysis buffer (25 mM Tris chloride pH 7.8, mM EDTA, 8 mM magnesium chloride, 1% Triton X-100, 1 mM DTT) for 10 min. The cell lysate mixture was scraped, transferred to 1.5 ml micro centrifuge tubes, and centrifuged for 7 min at 13,000 g at 4° C. to pellet debris.

Luciferase reporter gene expression was analyzed following transfection of HepG2 or COS 7 cells with peptide DNA condensates prepared at stoichiometries ranging from 0.1–1.5 nmol of peptide per µg of DNA. A ten-fold enhancement in the gene expression level was achieved when chloroquine was included in the transfecting media. For each peptide condensing agent, the maximal reporter gene expression occurred at a peptide/DNA stoichiometry that corresponds to the fully condensed DNA as determined by the asymptote in the light scattering assay (FIGS. 1D, E, F). At stoichiometries greater than that required to achieve condensation the gene expression remained constant. Thereby, the relative gene expression levels were compared for each peptide DNA condensate at a fixed stoichiometry of 0.8 or 1.0 nmol (SEQ ID NO:7) (DiCWK$_3$) of peptide per µg of DNA which was sufficiently for each peptide to fully condense DNA.

Lysis buffer (300 µl), sodium-ATP (4 µl of a 180 mM solution, pH 7, 4° C.) and cell lysate (100 µl, 4° C.) were combined in a test tube, briefly mixed and immediately placed in the luminometer. Luciferase relative light units (RLU) were recorded on a Lumat LB 9501 (Berthold Systems, Germany) with 10 sec integration after automatic injection of 100 µl of 0.5 mM D-luciferin (prepared fresh in lysis buffer without DTT). The RLU were converted into fmol using a standard curve generated each day using luciferase dissolved in Tris acetate pH 7.5 and stored at −20° C. The standard curve was constructed by adding a known amount of the enzyme (0.01–100 fmols with specific activity of 2.5 nU/fmol) to 35 mm wells containing 40–70% confluent HepG2 or COS 7 cells. The cells were processed as described above resulting in a standard curve with an average slope of 130,000 RLU per fmol of enzyme.

Protein concentrations were measured by Bradford assay using bovine serum albumin as a standard. The amount of luciferase recovered in each sample was normalized to milligrams of protein and the mean and standard deviation obtained from each triplicate are reported.

COS 7 cells were plated at 72,000 cells per well and grown to 50% confluency in DMEM (Gibco BRL) supplemented with penicillin (10,000 U/ml), L-glutamine (200 mM), and 10% FBS for 24 hrs. The cells were transfected as described for HepG2 cells.

Lipofectace™ (Gibco BRL, 1:2.5 w/w dimethyl dioctadecylammonium bromide and dioleoyl phosphatidylethanolamine) was used to mediate nonspecific gene transfection according to the manufacturer's instructions. The ratio of DNA to lipofectace was optimized for both COS 7 and HepG2 cells. An optimal DNA/lipofectace ratio was achieved by dissolving 10 µg of DNA in 100 µl of serum free media (SFM) followed by adding 60 µl of lipofectace prepared in 140 µl of SFM. The lipofectace DNA complex was then diluted with 1.7 ml of SFM and used to transfect HepG2 or COS 7 cells for 5 hrs followed by replacing the transfecting media with supplemented 10% FBS. The cells were incubated for a total of 24 hrs then harvested and analyzed for luciferase as described above.

Dose response curves were prepared by varying the dose from 1–50 µg of DNA while keeping the peptide/DNA stoichiometry fixed at 0.6 nmol per µg of DNA and normalizing the volume to 0.5 ml. Alternatively, a dose response curve for lipofectace was prepared by varying the DNA dose from 1–20 µg while keeping the stoichiometry of lipofectace to DNA constant and normalizing the total volume of each dose to 2 ml with SFM.

Figure 3A:
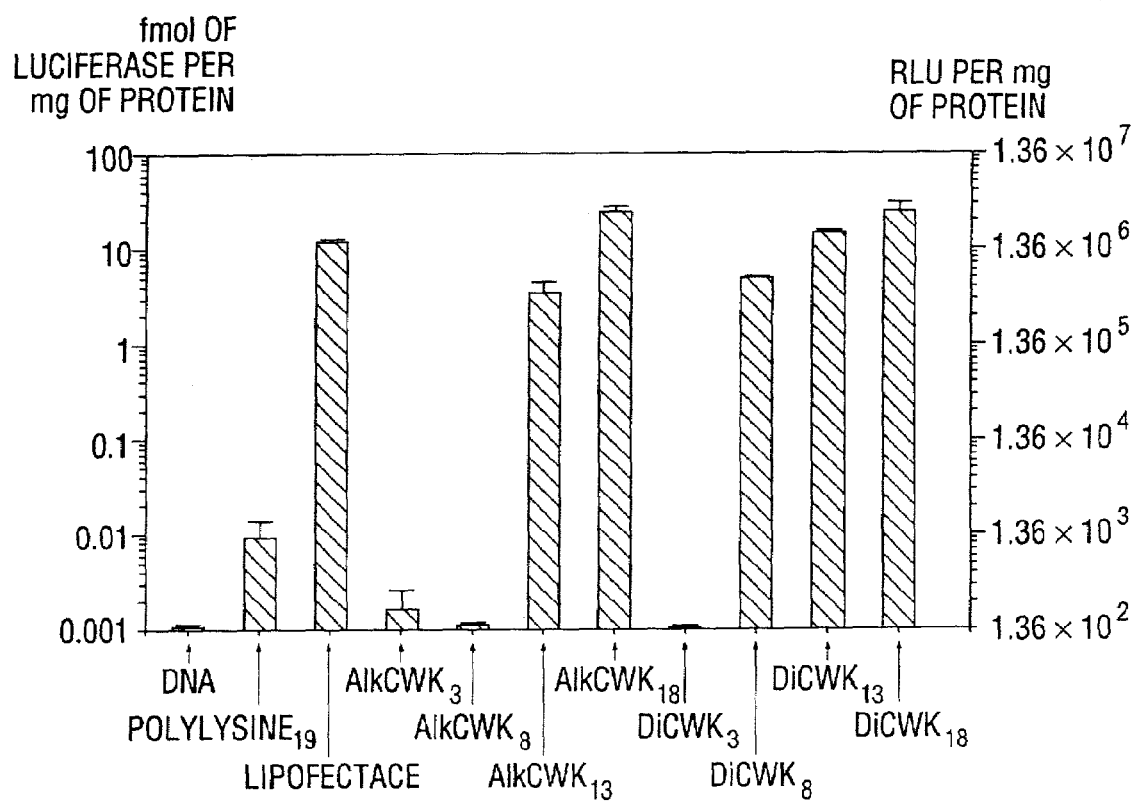
FIGS. 3A and 3B show reporter gene expression for DNA condensates.

Transfection of HepG2 with 10 µg of either uncomplexed DNA (SEQ ID NO:4; SEQ ID NO:5; SEQ ID NO:7; SEQ ID NO:2), AlkCWK$_{3\ or\ 8}$, DiCWK$_3$ or polylysine$_{19}$ DNA condensates failed to produce a significant reporter gene expression (FIG. 3A). This result supported formulation experiments that predicted these peptides either fail to condense DNA (SEQ ID NO:4) (AlkCWK$_3$) or produced condensates that were large (0.7–3.1 µm). Alternatively (SEQ ID NO:6; SEQ ID NO:3), AlkCWK$_{13\ or\ 18}$ and (SEQ ID NO:8; SEQ ID NO:9; SEQ ID NO:10) DiCWK$_{8,\ 13\ or\ 18}$ DNA condensates each demonstrated significant gene transfer efficiency that was two to three orders of magnitude greater than (SEQ ID NO:2) polylysine$_{19}$. Lipofectace mediated gene expression levels were also found to be identical to peptide mediated expression levels in HepG2 cells (FIG. 3A).

Figure 3B:
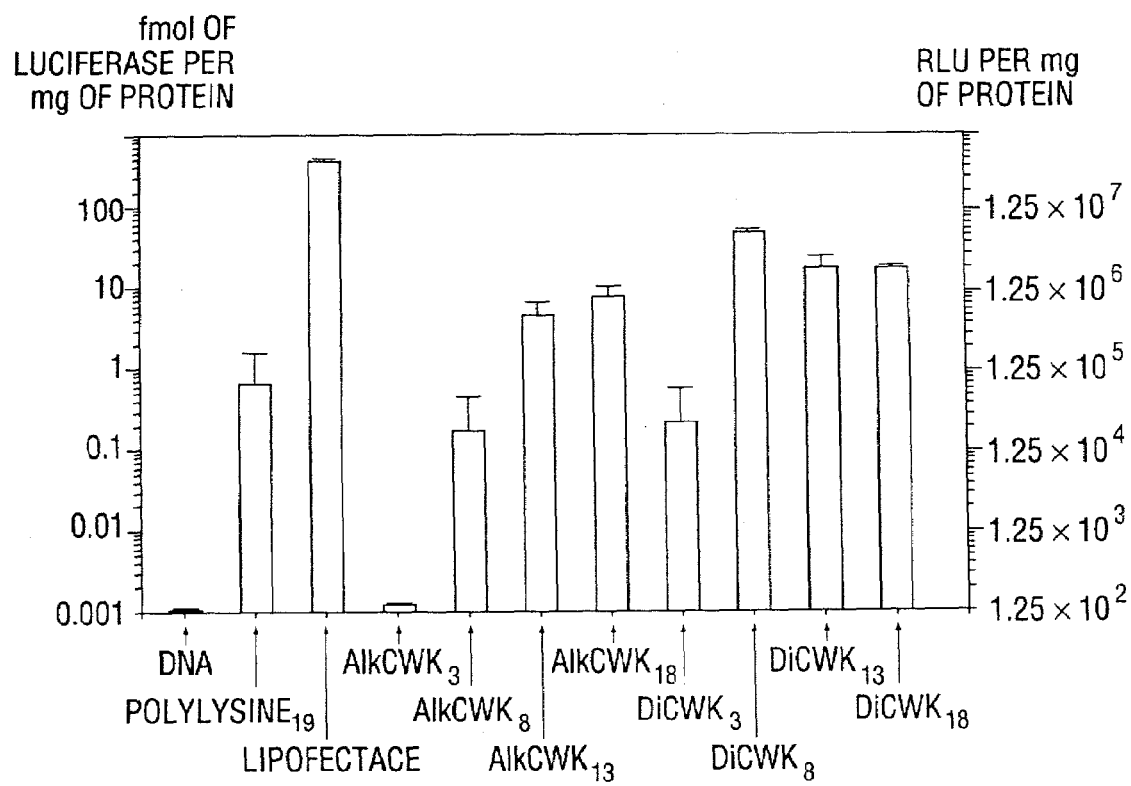

To verify that peptide mediated gene delivery was not dependent on the existence of cell type specific receptors, the reporter gene expression in HepG2 cells was compared to COS 7 cells (FIG. 3B). Significant differences were observed for the transfection of COS 7 versus HepG2 cells such that only uncomplexed DNA and (SEQ ID NO:4) AlkCWK$_3$ DNA condensates failed to produce measurable gene expression levels. AlkCWK$_8$ (SEQ ID NO:5; SEQ ID NO:7; SEQ ID NO:2), DiCWK$_3$ and polylysine$_9$ DNA condensates each mediated a significant gene expression in COS 7 cells despite their inactivity in transfecting HepG2 cells. However, the gene expression level mediated by these peptides was still one to two orders of magnitude below that afforded by (SEQ ID NO:6; SEQ ID NO:3) AlkCWK$_{13\ or\ 18}$ (SEQ ID NO:8; SEQ ID NO:9; SEQ ID NO:10) and DiCWK$_{8,\ 13\ and\ 18}$ (FIG. 3B). Also, lipofectace mediated gene expression in COS 7 cells was one order of magnitude greater than peptide mediated gene delivery. These results suggest that the size restriction of peptide DNA condensates is less stringent in COS 7 cells compared to HepG2 cells.

Figure 4:
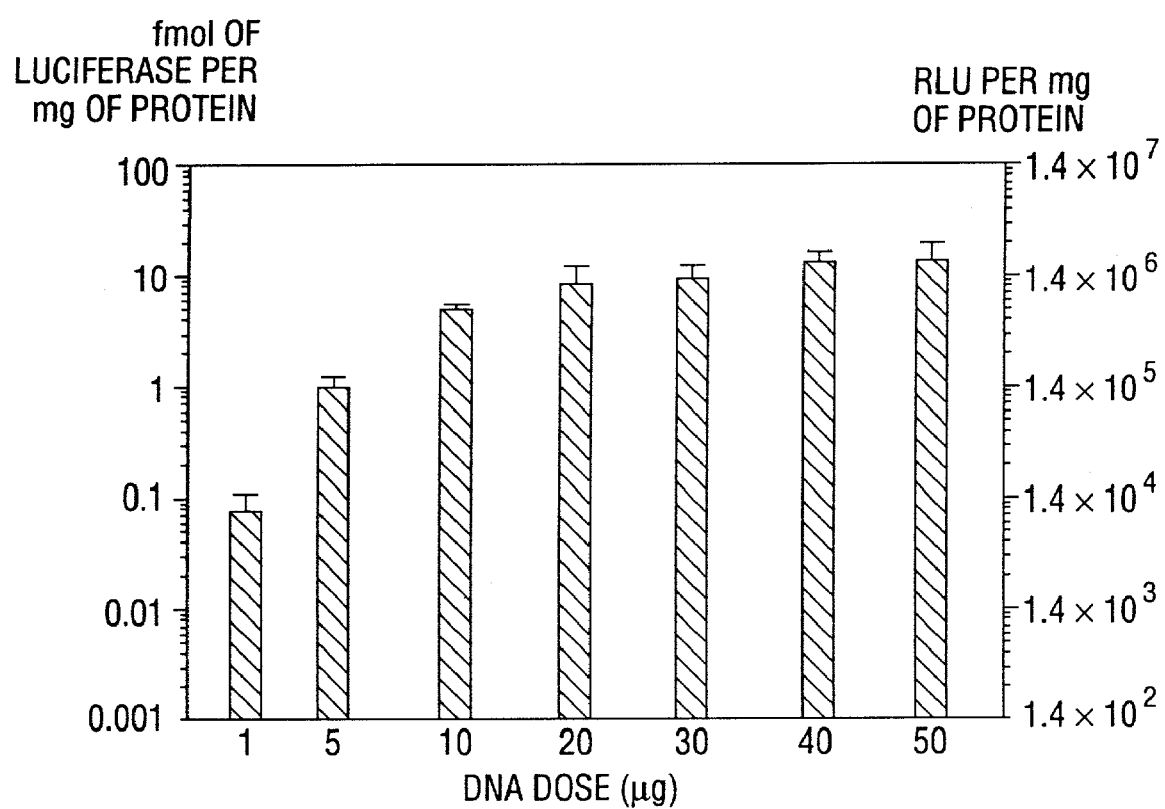
FIG. 4 is a dose response curve showing gene expression in HepG2 cells.

To establish the effect of dose response using peptide DNA condensates, HepG2 cells were treated with escalating doses of (SEQ ID NO:3) AlkCWK$_{18}$ DNA condensates and lipofectace DNA formulations. As demonstrated in FIG. 4, a dose response curve for the (SEQ ID NO:3) AlkCWK$_{18}$ DNA condensate plateaus at 20 µg of DNA and remains constant at higher doses whereas the toxicity of lipofectace appears above 10 µg of DNA (data not shown) and leads to reduced expression levels at higher doses.

From the above, it should be evident that the present invention provides compositions and methods that allow for efficient gene delivery. The development of homogenous peptides that actively condense DNA into small particles is an important advance. Attachment of a receptor ligand such as a carbohydrate or peptide to a single cysteine residue provides specificity to the gene delivery system. The above methods and compositions are amenable to use with virtually any gene of interest and permit the introduction of genetic material into a variety of cells and tissues.

The invention claimed is:

1. A tryptophan-containing peptide of less than forty amino acids in length that binds to nucleic acid, wherein said peptide comprises tryptophan, a cysteine and a lysine repeat from between 3 and 36 residues.

2. The peptide of claim 1, wherein said peptide comprises 13–18 lysine residues.

3. The peptide of claim 1, wherein said peptide is less than thirty amino acids in length.

4. The peptide of claim 1, wherein said peptide is bound to nucleic acid encoding one or more gene products to make a complex.

5. The peptide of claim 1, wherein said Cys is an N-terminal cysteine that is alkylated.

6. The peptide of claim 3, wherein said peptide is less than twenty amino acids in length.

7. The peptide of claim 1, wherein said peptide comprises 13 lysine residues.

8. The peptide of claim 1, wherein said peptide comprises 18 lysine residues.

9. The peptide of claim 1, wherein said peptide comprises 16 lysine residues.

10. The peptide of claim 1, wherein said peptide comprises 26 lysine residues.

11. The peptide of claim 1, wherein said peptide comprises 36 lysine residues.

12. The peptide of claim 1, wherein said peptide comprises two tryptophan residues.

13. The peptide of claim 4, wherein said nucleic acid is from a viral source.

14. The peptide of claim 4, wherein said nucleic acid is from a bacterial source.

15. The peptide of claim 4, wherein said nucleic acid is from an animal source.

16. The peptide of claim 4, wherein said nucleic acid is from a plant source.

17. A method comprising:
  a) providing: i) nucleic acid encoding one or more gene products; ii) a tryptophan—containing peptide of less than forty amino acids in length that binds to said nucleic acid, wherein said peptide comprises tryptophan, a cysteine and a lysine repeat from between 3 and 36 residues; and iii) a cell having a cell membrane;
  b) binding said tryptophan—containing peptide to said nucleic acid to make a complex;
  c) introducing said complex to said cell under conditions such that said complex is delivered across said cell membrane.

18. The method of claim 17, wherein said peptide comprises 13–18 lysine residues.

19. The method of claim 17, wherein said peptide comprises 13 lysine residues.

20. The method of claim 17, wherein said peptide comprises 18 lysine residues.

21. The method of claim 17, wherein said peptide comprises 16 lysine residues.

22. The method of claim 17, wherein said peptide comprises 26 lysine residues.

23. The method of claim 17, wherein said peptide comprises 36 lysine residues.

24. The method of claim 17, wherein said peptide comprises two tryptophan residues.

25. The method of claim 17, wherein said peptide is less than thirty amino acids in length.

26. The method of claim 25, wherein said peptide is less than twenty amino acids in length.

27. The method of claim 17, wherein said nucleic acid is from a viral source.

28. The method of claim 17, wherein said nucleic acid is from a bacterial source.

29. The method of claim 17, wherein said nucleic acid is from an animal source.

30. The method of claim 17, wherein said nucleic acid is from a plant source.

* * * * *

UNITED STATES PATENT AND TRADEMARK OFFICE
CERTIFICATE OF CORRECTION

| | |
|---|---|
| PATENT NO. | : 7,112,442 B2 |
| APPLICATION NO. | : 10/108844 |
| DATED | : September 26, 2006 |
| INVENTOR(S) | : Kevin G. Rice et al. |

It is certified that error appears in the above-identified patent and that said Letters Patent is hereby corrected as shown below:

On the First Page:

At Item (73), "Ann Harbor" should be -- Ann Arbor --.

Signed and Sealed this

Third Day of April, 2007

JON W. DUDAS
*Director of the United States Patent and Trademark Office*